(12) United States Patent
Krahl et al.

(10) Patent No.: US 9,421,363 B2
(45) Date of Patent: Aug. 23, 2016

(54) SYSTEMS AND DEVICES FOR CRAINIAL IMPLANTATION OF A NEUROMODULATION DEVICE

(75) Inventors: Scott E. Krahl, Stevenson Ranch, CA (US); Antonio A. F. De Salles, Los Angeles, CA (US)

(73) Assignees: THE REGENTS OF THE UNIVERSITY OF CALIFORNIA, Oakland, CA (US); THE UNITED STATES OF AMERICA GOVERNMENT DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 13/574,532

(22) PCT Filed: Jan. 19, 2011

(86) PCT No.: PCT/US2011/021760
§ 371 (c)(1),
(2), (4) Date: Oct. 11, 2012

(87) PCT Pub. No.: WO2011/091071
PCT Pub. Date: Jul. 28, 2011

(65) Prior Publication Data
US 2013/0030368 A1 Jan. 31, 2013

Related U.S. Application Data

(60) Provisional application No. 61/296,566, filed on Jan. 20, 2010.

(51) Int. Cl.
*A61N 1/05* (2006.01)
*A61M 25/02* (2006.01)
*A61M 39/02* (2006.01)

(52) U.S. Cl.
CPC ............ *A61N 1/0539* (2013.01); *A61M 25/02* (2013.01); *A61B 2090/103* (2016.02); *A61M 2025/0213* (2013.01); *A61M 2025/0246* (2013.01); *A61M 2039/025* (2013.01)

(58) Field of Classification Search
CPC .............. A61N 1/0539; A61M 25/02; A61M 2039/025; A61M 2025/0246; A61B 2090/103
USPC ............... 604/890.1, 891.1, 533, 288.1, 175; 607/45, 46, 115, 116; 600/386
See application file for complete search history.

(56) References Cited

U.S. PATENT DOCUMENTS 6,006,124 A  12/1999 Fischell et al.
6,427,086 B1  7/2002 Fischell et al.
(Continued)

*Primary Examiner* — Theodore Stigell
*Assistant Examiner* — Benjamin Koo
(74) *Attorney, Agent, or Firm* — Vista IP Law Group LLP

(57) ABSTRACT

Described herein is an implantable device including: a housing including a connection opening defined therein, wherein the connection opening includes posts and slots and is configured to receive at least one connection associated with a neuromodulation device; a connection holding cap having posts, wherein the posts are configured to oppose the posts of the connection opening and wherein the connection holding cap is configured to receive the at least one connection associated with the neuromodulation device and configured to be operably connected to the connection opening by interconnecting the opposing posts after receiving the at least one connection associated with the neuromodulation device; a neuromodulation device holder operably connected to the device housing and configured to receive the neuromodulation device and secure the neuromodulation device within the device housing; and a cover operably connected to the device housing and configured to seal the device housing. Other embodiments are also described.

9 Claims, 7 Drawing Sheets

(56) References Cited

U.S. PATENT DOCUMENTS

| | | |
|---|---|---|
| 8,038,685 B2 * | 10/2011 | Bedenbaugh ................ 606/130 |
| 8,442,644 B2 * | 5/2013 | Stevenson et al. ............ 607/60 |
| 2002/0052610 A1 * | 5/2002 | Skakoon et al. ............. 606/129 |
| 2004/0176814 A1 | 9/2004 | Singhal et al. |
| 2005/0070971 A1 | 3/2005 | Fowler et al. |
| 2006/0195154 A1 | 8/2006 | Jaax et al. |
| 2006/0212090 A1 * | 9/2006 | Lozano et al. ................. 607/45 |
| 2009/0112277 A1 * | 4/2009 | Wingeier et al. .............. 607/45 |
| 2009/0112279 A1 | 4/2009 | Wingeier et al. |

* cited by examiner

SYSTEMS AND DEVICES FOR CRAINIAL IMPLANTATION OF A NEUROMODULATION DEVICE

CROSS REFERENCE TO RELATED APPLICATIONS

This Application is a U.S. National Stage filing under 35 U.S.C. §371 of International PCT Application No. PCT/US2011/021760, filed Jan. 19, 2011, which claims priority to U.S. Provisional Patent Application Ser. No. 61/296,566, entitled "Systems, Devices and Methods for Cranial Implantation of a Neuromodulation Device" filed on Jan. 20, 2010, and which are hereby incorporated by reference in its entirety.

STATEMENT REGARDING FEDERALLY SPONSORED RESEACH OR DEVELOPMENT

This work was supported by the U.S. Department of Veterans Affairs, and the Federal Government has certain rights in the invention.

INCORPORATION-BY-REFERENCE OF MATERIAL SUBMITTED ON A COMPACT DISC

Not Applicable

FIELD

The present disclosure generally relates to medical apparatus and methods, and more particularly relates to systems and devices for the cranial implantation of neuromodulation devices and methods of implanting and using the same.

BACKGROUND

In general, neuromodulation refers to the modulation of the nervous system. Neuromodulation may include medical procedures that alter or modulate the function of the nervous system in order to, for example, treat a disease or provide pain relief. The medical procedures may include providing electrical stimulation by, for example, an implantable pulse generator (IPG) or a transcutaneous electrical nerve stimulation (TENS) device, lesioning of specific regions of the nervous system, or the infusion of substances (e.g. pharmaceutical drugs) into the cerebrospinal fluid or brain tissue by, for example, a drug infusion pump.

Deep brain stimulation (DBS) is a surgical treatment involving the implantation of a medical device, similar to a pacemaker, which sends electrical impulses to specific parts of the brain. DBS directly changes brain activity in a controlled manner and its effects are reversible (unlike those of lesioning techniques).

Generally, the DBS system consists of three components: the IPG, at least one electrode (or "lead"), and at least one extension. The IPG is a battery-powered neurostimulator which sends electrical pulses to the brain to modulate neural activity at the target site. The electrode may be a coiled wire insulated in polyurethane terminating with multiple platinum iridium contacts and is placed in or on the target area of the brain. Electrodes are placed in the brain according to the type of symptoms to be addressed.

In some cases, all three components of the DBS system are surgically implanted inside the body. Typically, the electrode is connected to the IPG by the extension, an insulated wire that runs from the head and down the side of the neck behind the ear to the IPG, which may be placed subcutaneously below the clavicle or in some cases, the abdomen. The IPG may be calibrated to optimize symptom suppression and control side effects.

Implantable drug infusion systems generally include drug infusion pumps and catheters. The pump is generally implanted in the patient's abdomen and the catheter, which is connected to the pump, is implanted in the space surrounding the spinal cord. For example, an intrathecal pump includes a metal pump which stores and delivers the drug, and a catheter which delivers the drug from the pump to the intrathecal space in the spine. Generally, there are two types of pumps: a programmable pump which delivers the drug at a rate determined by a programmable computer program (or according to instructions provided to the computer by a clinician) and a constant rate pump which delivers the drug at a constant rate. The catheter may also be inserted into the brain to deliver the drug into the cerebral spinal fluid or the brain tissue.

IPGs and implantable drug infusion systems are designed to have long lifetimes or to be easily rechargeable. However, the connections between the pump device and the infusion site or the IPG and the site of modulation are under the patient's skin. This may cause the patient discomfort and the device (IPG or pump) may be more susceptible to the failure of its hardware, or to erosion of the patient's skin covering its parts or connections, thereby increasing the risk of patient infection.

Therefore, a need exists for devices and systems for the implantation of neuromodulation devices that reduce patient discomfort and risk of infection and reduce the risks of device hardware failure or skin erosion.

The information included in this Background section of the specification, including any references cited herein and any description or discussion thereof, is included for technical reference purposes only and is not to be regarded as subject matter by which the scope of the invention is to be bound.

SUMMARY

One aspect of the subject matter of the present disclosure addresses the aforementioned needs by providing a method for implantation of a neuromodulation device into a patient's cranium. In one aspect, the method may include: implanting in the patient's cranium a device housing of an implantable device, the implantable device comprising: a device housing having a connection opening defined therein, a neuromodulation device holder, a connection holding cap, and a cover; introducing at least one connection associated with the neuromodulation device through the connection opening defined in the device housing; securing the connection about the connection opening; operably attaching the connection holding cap to the connection opening; introducing the neuromodulation device into the device housing; operably connecting the neuromodulation device holder to a distal end of the device housing to secure the neuromodulation device within the neuromodulation device holder; and operably connecting the cover to the device housing and the patient's cranium to close the implantable device. In one aspect of the method, the neuromodulation device is an implantable pulse generator and the at least one connection associated with the neuromodulation device is an electrode. The method may further comprise placing excess wire associated with the neuromodulation device into the device housing.

In another aspect of the method, the neuromodulation device is an implantable drug delivery system and the at least one connection associated with the neuromodulation device is a catheter. The method may further comprise placing excess catheter associated with the neuromodulation device into the device housing.

In another aspect of the present disclosure, a system for implantation of a neuromodulation device into a patient's cranium is disclosed. The system may include a neuromodulation device having at least one connection associated therewith; an implantable device comprising: a device housing comprising a connection opening defined therein and configured to receive the at least one connection associated with the neuromodulation device, a cover, a connection holding cap configured to receive the at least one connection associated with the neuromodulation device and configured to be operably connected to the connection opening after receiving the at least one connection associated with the neuromodulation device, and a neuromodulation device holder operably connected to the implantable device and configured to receive the neuromodulation device and secure the neuromodulation device within the implantable device; a connection clamp operably connected with the at least one connection associated with the neuromodulation device, wherein the connection clamp secures the at least one connection in a slot at an outer circumference of the connection opening; a connection clamp applicator for operably connecting the connection clamp to the connection opening; and at least one coupling device operably connecting the implantable device to the patient's cranium.

In one aspect of the system, the neuromodulation device is an implantable pulse generator and the at least one connection associated with the neuromodulation device is an electrode. In one aspect of the system, the neuromodulation device is an implantable drug delivery system and the at least one connection associated with the neuromodulation device is a catheter.

In still another aspect of the disclosure, an implantable device configured for receiving a neuromodulation device is disclosed. The implantable device may include a device housing comprising: a connection opening defined therein, wherein the connection opening includes posts and slots and is configured to receive the at least one connection associated with the neuromodulation device; a connection holding cap comprising posts, wherein the posts are configured to oppose the posts of the connection opening and wherein the connection holding cap is configured to receive the at least one connection associated with the neuromodulation device and configured to be operably connected to the connection opening by interconnecting the opposing posts after receiving the at least one connection associated with the neuromodulation device; a neuromodulation device holder operably connected to the device housing and configured to receive the neuromodulation device and secure the neuromodulation device within the device housing; and a cover operably connected to the device housing and configured to close the device housing in the patient's cranium.

In one aspect of the device, the neuromodulation device is an implantable pulse generator and the at least one connection associated with the neuromodulation device is an electrode. In one aspect of the device, the neuromodulation device is an implantable drug delivery system and the at least one connection associated with the neuromodulation device is a catheter.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

BRIEF DESCRIPTION OF THE DRAWINGS

The present disclosure may be understood by reference to the following description, taken in connection with the accompanying drawings, in which.

DETAILED DESCRIPTION

The present disclosure relates to devices and systems configured for cranial implantation of a neuromodulation device. More specifically, the present disclosure relates to devices and systems configured for cranial implantation of an implantable pulse generator (IPG) or implantable drug infusion system. Methods of implanting the device and system in the cranium are also disclosed. Kits including the systems and/or devices configured for cranial implantation of an IPG or implantable drug infusion system are also disclosed. The systems and devices disclosed herein house energy delivering or recording devices (IPGs) or drug delivery (infusion) systems inside the matter of the skull vault thereby eliminating or at least reducing the need for the connections or wires associated with IPGs or drug infusion systems to be placed under the scalp or the skin.

The following description is provided to enable any person skilled in the art to make and use the subject matter of this disclosure, and it sets forth the best modes contemplated by the inventors of carrying out the various aspects of the disclosure. Various modifications, however, will remain readily apparent to those skilled in the art, since the general principles of the disclosed subject matter have been defined herein specifically to describe: (1) systems and devices configured for cranial implantation of a neuromodulation device, such as an IPG or implantable drug infusion system; (2) methods of implanting the device and/or system in the cranium; and (3) kits including the device and system configured for cranial implantation of a neuromodulation device.

Figure 1:
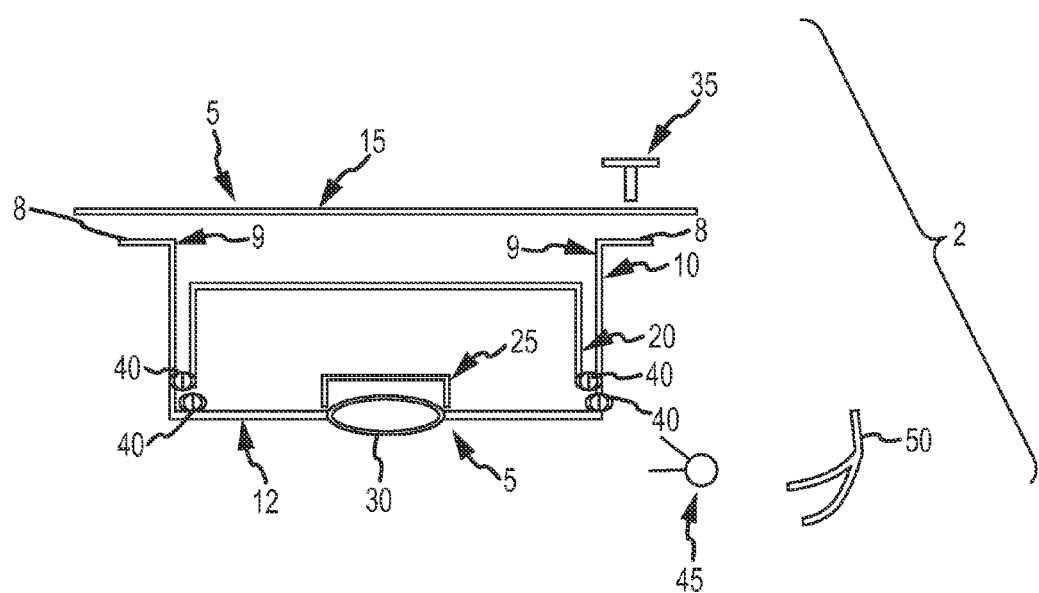
FIG. 1 depicts one embodiment of a system configured for cranial implantation of a neuromodulation device.
Figure 2:
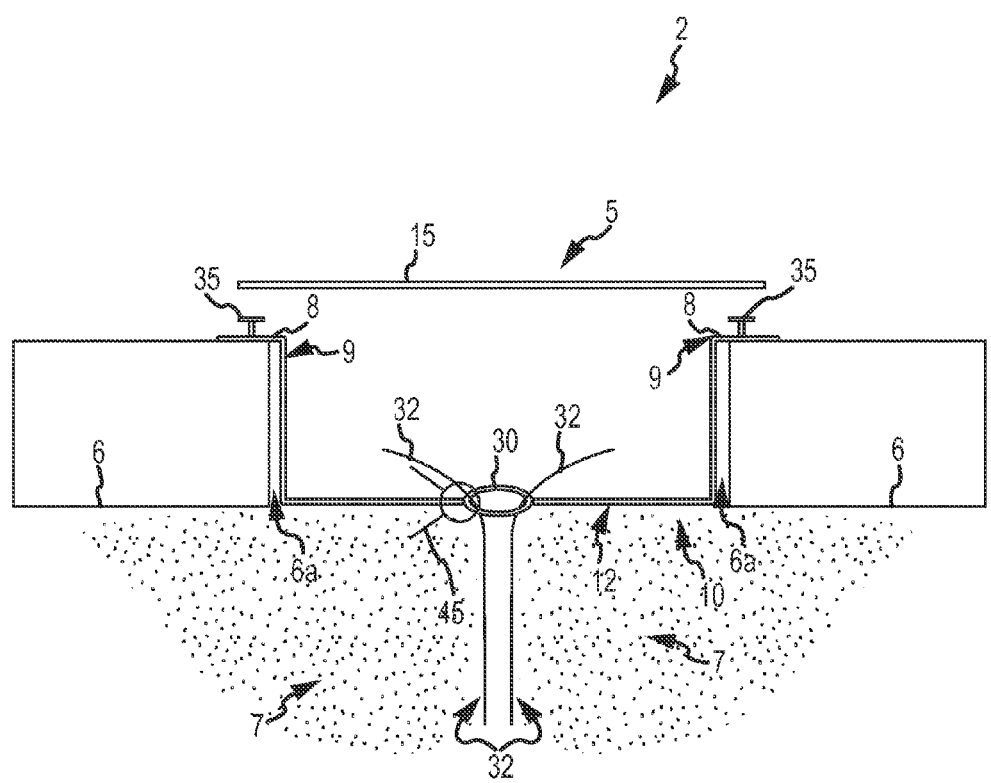
FIG. 2 depicts a cross section of a patient's skull showing a housing and a cover of an implantable device of the system of FIG. 1 implanted therein.
Figure 3A:
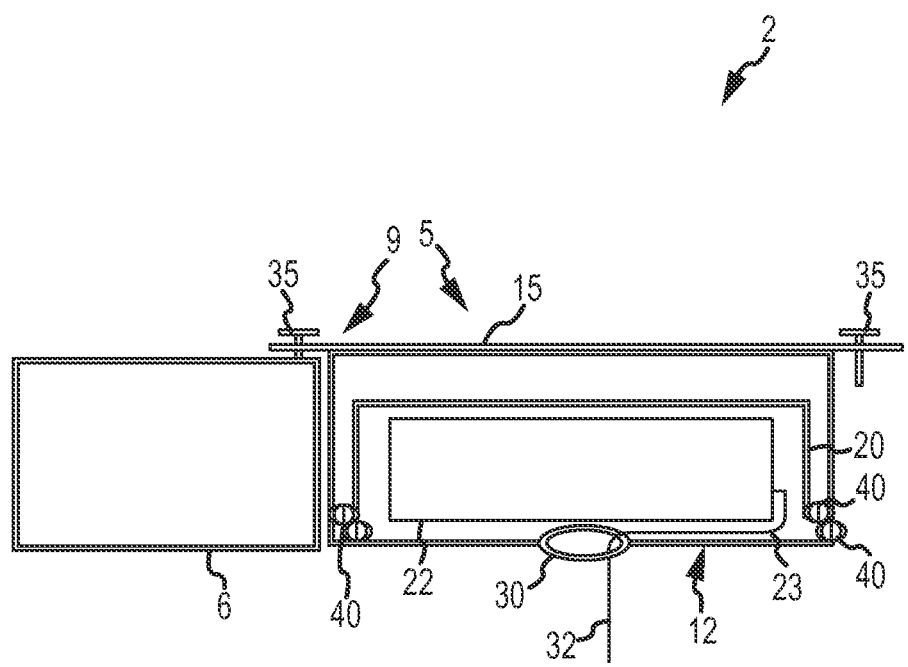
FIG. 3A is the same view as depicted in FIG. 2, wherein an IPG and a generator holder are shown and part of the skull is not shown for clarity purposes.
Figure 3B:
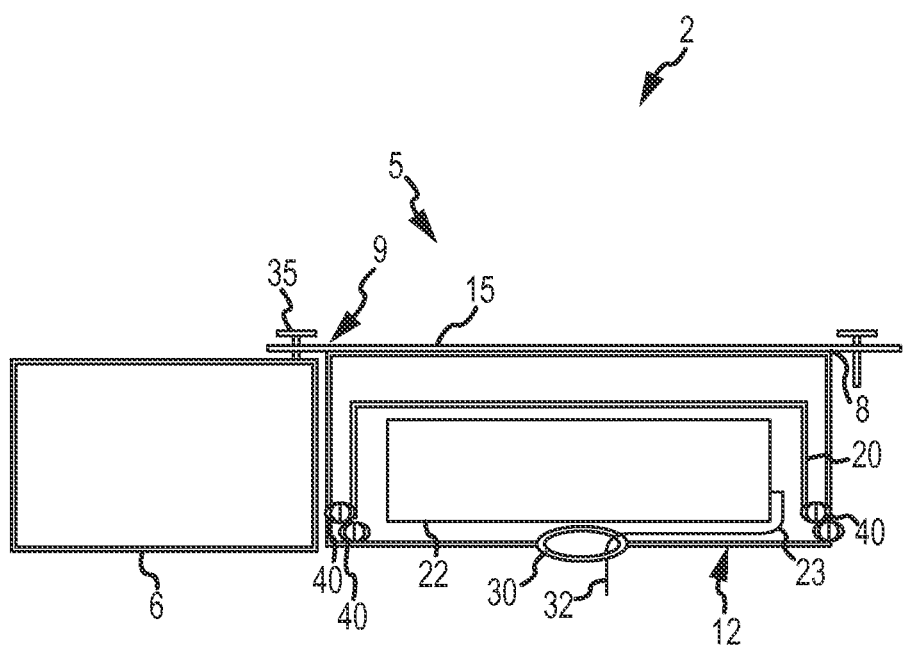
FIG. 3B is the same view of the skull as depicted in FIG. 2 except another embodiment of the system and device of FIG. 1 including a drug infusion pump and a pump holder is shown and part of the skull is not shown for clarity purposes.

For a general description of a system and device configured for cranial implantation of a neuromodulation device, reference is first made to FIGS. 1-3B, which illustrate various components of the system 2, which comprises the implantable device 5. As can be understood from FIGS. 1-3B, the system 2 may include an implantable device 5 including a housing device 10 with a cover 15, a neuromodulation device holder 20 and a connection holding cap 25. As shown in FIGS. 3A-3B, the system 2 also includes a neuromodulation device 22. In some embodiments, as indicated in FIG. 1, the system 2 may also include coupling devices, such as self tapping screws 35, securing devices 40, a clamp 45 and a clamp applicator 50.

As shown in FIGS. 1 and 2, the implantable device 5 includes a cover 15 and a housing device or device housing 10. The cover 15 is configured to be received by the border of the craniotomy 6a (e.g. the outer table of the skull 6), thereby enclosing the housing device 10 and a neuromodulation device 22 (as shown in FIGS. 3A-3B). In some embodiments, the cover 15 is approximately 50mm. In other embodiments, the cover 15 is greater than or less than 50mm depending upon the general dimensions of the housing device 10 and the location of the border (outer table) of the craniotomy 6a, as the cover 15 will enclose the housing device 10, and the housing device 10 and cover 15 will be secured to the border of the craniotomy 6a via a coupling device, such as self tapping screws 35. It can be appreciated that the housing device 10 and cover 15 may be operably connected to the outer table of the skull 6 by any other appropriate coupling devices known to those of skill in the art.

The housing device or device housing 10 of the implantable device 5 may be a platform or dish shape and is configured to be received in the space between the inner and outer skull surfaces of a patient, thereby providing access to the patient's brain 7. In some embodiments, as shown in FIG. 1, the device housing 10 is a three-sided platform or three-sided box. In other embodiments, the housing 10 is more rounded or dish-shaped to follow the curvature of the skull at the site of implantation.

As shown in FIGS. 2-3B, the distal end or brain side 12 of the housing device 10 includes at least one connection opening 30 configured to receive at least one connection 32, such as an electrode or a catheter, associated with a neuromodulation device and to facilitate passage of the connection 32 between the neuromodulation device housed in the housing device 10 and the patient's brain 7. The connection opening 30 may be in the relative center of the distal end 12 of the device 10. In other embodiments, the connection opening 30 may be in any location in the distal end 12 of the device 10 to facilitate passage of the at least one connection 32 through the connection opening 30.

As indicated in FIGS. 1-3B, the proximal end 9 of the housing device 10 includes a fringe or a lip feature 8 configured to operably connect the device 10 to an outer table of the skull 6 (craniotomy) via a coupling device, such as self tapping screws 35. It can be appreciated that the lip feature 8 of the housing device 10 may be operably connected to the outer table of the skull 6 by any other appropriate coupling devices known to those of skill in the art.

As discussed in more detail below with respect to FIGS. 3A and 3B, the housing device 10 is configured to receive a neuromodulation device, thereby housing (and protecting) the neuromodulation device while providing a generally imperceptible profile for the implantable device 5 (i.e., flush or nearly flush to the skull surface). The housing device 10 may be designed to accommodate the general measurements to house most neuromodulation devices. In one embodiment, the housing device 10 is approximately 13mm in height and approximately 50mm in width. In some embodiments, the height of the housing device 10 is slightly less than the thickness of the skull (approximately 15 mm). In some embodiments, the housing device 10 is custom designed in dimension and/or shape to accommodate specific neuromodulation devices.

The housing device 10 and cover 15 of the implantable device 5 are MRI compatible and may be made of plastic, ceramic, or a metal alloy or a combination thereof. In embodiments where the neuromodulation device is an IPG, such MRI compatibility allows the clinician to check the position of the electrodes before placement or attachment of the IPG. The housing device 10, cover 15 and neuromodulation device holder 20 can also be constructed to insulate the IPG from the magnetic field of a MRI.

As can be understood from FIGS. 1 and 3A-3B, the implantable device 5 also includes a neuromodulation device holder 20. The neuromodulation device holder 20 is configured to maintain or secure the neuromodulation device 22 within the implantable device 5 and reduce or prevent movement of the neuromodulation device 22 after implantation. In some embodiments, the neuromodulation device holder 20 may be configured to receive an IPG. In some embodiments, the neuromodulation device holder 20 may be configured to receive an implantable drug infusion system.

As shown in FIGS. 3A-3B, the system 2 also includes a neuromodulation device 22. The system 2 may also include at least one connection 32 associated with the neuromodulation device 22. In some embodiments, the neuromodulation device 22 is an IPG and the connection 32 is an electrode 32 (See FIG. 3A). The IPG may be any available IPG device, such as the Activa system manufactured by Medtronic, Minneapolis, Minn., or the Brio or Libra systems manufactured by St. Jude Medical, Plano, Tex., or any other commercially available IPG. In some embodiments, the neuromodulation device 22 is an implantable drug infusion system and the connection 32 is a catheter (See FIG. 3B). The implantable drug infusion system may be any implantable drug infusion system, such as the SynchroMed II or SynchroMed EL drug infusion systems, both manufactured by Medtronic, Minneapolis, Minn., or any commercially available drug infusion device. In some embodiments, and as can be understood from FIG. 2, the connection 32 associated with the neuromodulation device 22 is placed at its respective insertion or infusion site(s) in the brain 7 prior to being connected with the neuromodulation device 22.

As can be understood from FIGS. 1 and 3A-3B, after placement of the connection(s) 32 in the brain, the neuromodulation device 22 may be introduced into the implantable device 5. The neuromodulation device holder 20 is placed over the neuromodulation device 22 and the holder 20 is secured to the distal end 12 of the housing device 10 by coupling devices such as securing devices 40, which may be screws, bolts or other appropriate coupling devices.

As indicated on FIGS. 3A and 3B, excess connections 23, such as excess wire or catheter, may be connected to the neuromodulation device 22. The excess connections 23 are housed within the implantable device 5.

Figure 4:
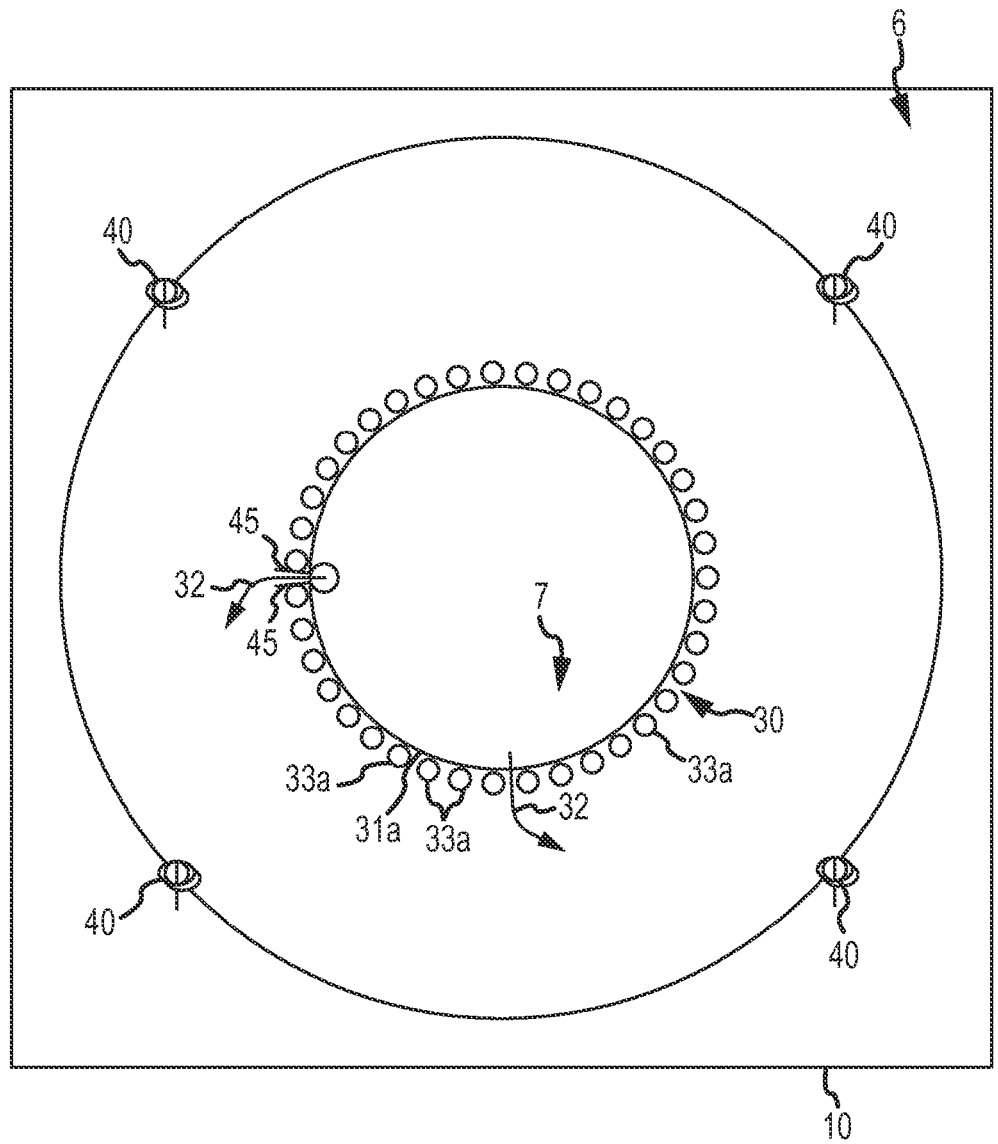
FIG. 4 depicts a top side or proximal end view of the housing as shown in FIG. 2, wherein a connection holding cover is also shown.
Figure 5:
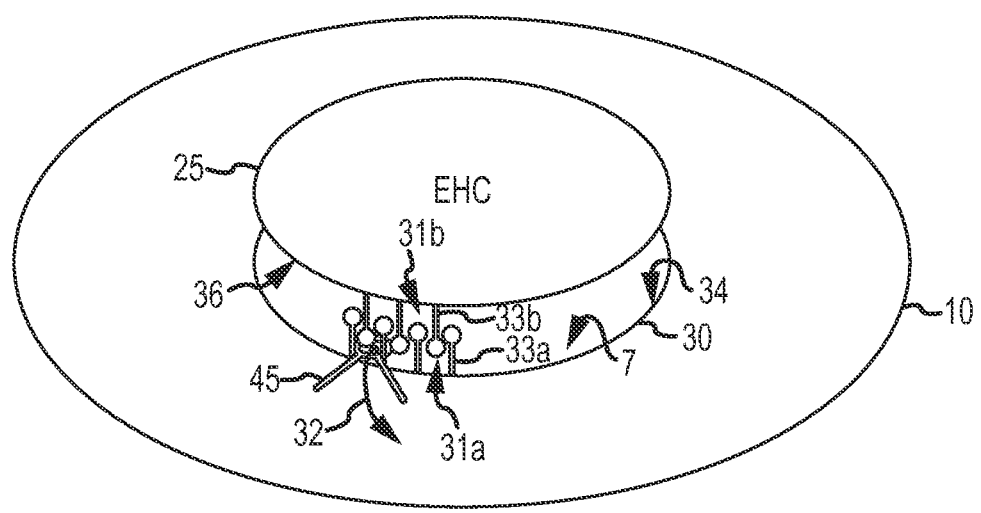
FIG. 5 is the housing and connection holding cover of FIG. 4, wherein posts located about the outer circumference of the connection opening and connection holding cover, respectively, are shown.

For a more detailed discussion of the mechanisms utilized to maintain the connections 32 in place after implantation in the target site (insertion site or infusion site, as applicable), reference is now made to FIGS. 4 and 5 (and with reference to FIG. 1), which illustrate the clamp 45, clamp applicator 50 and connection holding cap or cover 25 in use as well as other components of the system 2 and device 5.

As can be understood from FIGS. 4 and 5, and with reference to FIG. 1, the system 2 also includes a clamp 45 and a clamp applicator 50. In some embodiments, the clamp 45 may be an electrode clamp 45. In some embodiments, the clamp 45 may be a catheter clamp 45.

For ease of the reader, the following description is illustrated with the use of an electrode. However, the device and system described herein may also be used with a catheter. Accordingly, the description found below is to be considered illustrative in nature and not limiting.

As shown in FIGS. 4 and 5, and with reference to FIGS. 1 and 2, the device 10 includes a connection opening 30 and a connection holding cover or cap 25. As illustrated in FIGS. 4 and 5, the connection opening 30 includes radially spaced posts 33a with slots 31a therebetween about the outer circumference 34 of the connection opening 30. The radially spaced posts 33a are spaced apart such that the slots 31a therebetween are configured to receive opposing posts 33b (also radially spaced) located about the connection holding cover 25. When the opposing posts 33b are received in the slots 31a, the posts 33a, 33b form an interlocking pattern as shown in FIG. 5.

As best understood from FIG. 5, the connection holding cap 25 includes opposing posts 33b with slots 31b (which are both also radially spaced) therebetween about the outer circumference 36 of the connection holding cap 25. The opposing posts 33b are spaced apart such that the slots 31b therebetween are configured to receive radially spaced posts 33a located about the connection opening 30. When the radially spaced posts 33a are received in the slots 31b, the posts 33a, 33b form an interlocking pattern as shown in FIG. 5.

In use, and as shown in FIGS. 4 and 5, an electrode 32 is navigated through the connection opening 30 and through slots 31a between posts 33a of the connection opening 30. In some embodiments, the electrode 32 has been placed in the brain 7 at an insertion site prior to placement of the implantable device 5. In other embodiments, the electrode 32 is placed in the brain 7 at an insertion site after placement of the implantable device 5. Regardless of when the electrode is placed at the insertion site, once the electrode is navigated through the slots 31a of the connection opening 30, the electrode clamp 45 is utilized to maintain the electrode in place. In some embodiments, the clamp 45 may be a side pressure clamp attached to posts 33a of the connection opening 30 to hold the electrode in place. In some embodiments, the clamp 45 may be a side pressure clamp attached at or about the connection opening 30 to hold the electrode in place. The clamp applicator 50 is configured to aid in the placement of the clamp 45. For illustration purposes, FIG. 4 shows both an electrode 32 prior to placement of a clamp and with the electrode clamp 45 in place.

Once the clamps 45 are in place, the opposing posts 33b, 33a of the connection holding cap 25 and connection opening 30, respectively, are brought into contact with each other. Upon receipt of the opposing posts, which creates an interlocking pattern, the connection opening 30 is closed and the electrode(s) 32 are secured within the slots 31a. Thus, the electrode is held in place initially by the clamp 45 and then by the pressure induced when the connection opening 30 and connection holding cover 25 are sealed or otherwise secured together as described above. In some embodiments, the seal is a generally hermetic seal. In some embodiments, the seal is not a hermetic seal.

Next, the cover 15 of the implantable device 5 is secured to the implantable device 5 and the border of the craniotomy 6a by coupling devices, such as self tapping screws 35. Accordingly, the implantable device 5, including the IPG, and the electrodes 32 connected thereto, are secured, thereby reducing movement, within the craniotomy by the securing features described herein (e.g., the self tapping screws, the neuromodulation device holder, the connection holding cover (or cap) and the posts and slots of the connection opening).

Figure 6:
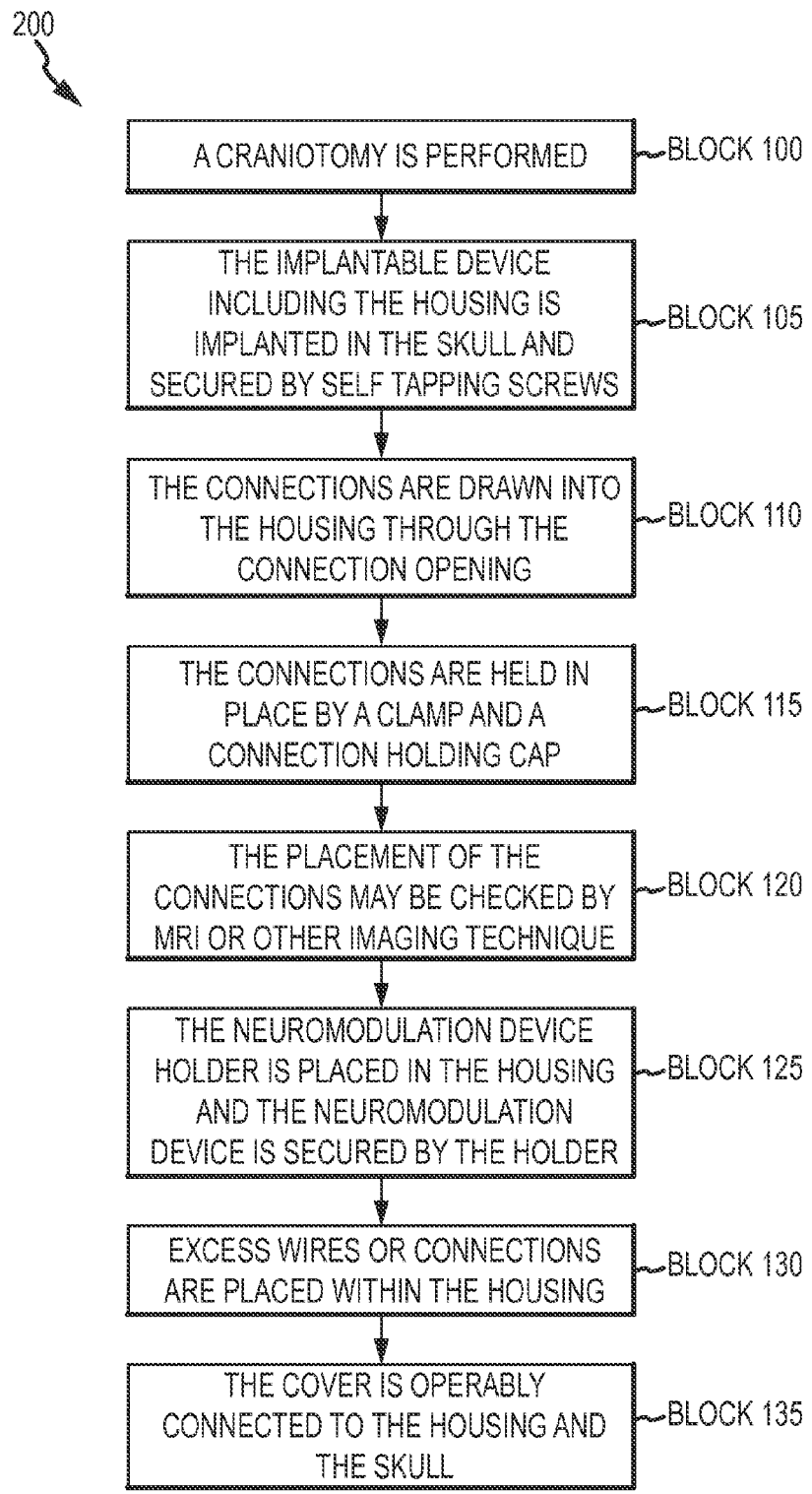
FIG. 6 illustrates a method for the cranial implantation of a neuromodulation device.

For a description of the method 200 of implanting components of the system 2 and the implantable device 5 as described herein, reference is now made to FIG. 6, which illustrates one embodiment of such a method. It should be appreciated that the operations of the method 200 may be performed in the order illustrated, in another suitable order and/or one or more operations may be performed simultaneously. Moreover, in some embodiments, the method 200 may include more or fewer operations than those illustrated.

A craniotomy is performed by any means known to one skilled in the art. (Block 100). The implantable device, including the housing is implanted in the skull and secured by self-tapping screws. (Block 105). The connection(s) is/are drawn into the housing 10 through the connection opening. (Block 110). The connection(s) is/are held in place by a clamp and a connection holding cap (cover). (Block 115). The placement of the connections may be checked by MRI or other imaging techniques. (Block 120). The neuromodulation device holder is placed in the housing and the neuromodulation device is secured by the holder. (Block 125). Excess wires or connections are placed within the housing. (Block 130). The cover is operably connected to the housing and the skull. (Block 135). It can be appreciated that certain steps may not be performed, such as the step in (Block 120), or certain steps may be done in a different order, such as reversing the order of steps described in (Block 120) and (Block 115), all without departing from the spirit and scope of the present disclosure.

The present disclosure is also directed to kits including the device 5, the system 2 or components thereof and instructions for use or implantation of the device 5 or the system 2 or components thereof.

In various embodiments, the kits may include a device or components of the system for the cranial implantation of a neuromodulation device. The kits may include the device 5 or system 2, or components thereof, as disclosed herein. The kits may also include any commercial IPGs (including but not limited to IPGs described herein) and any component parts (e.g. electrodes, wires, etc.). In alternative embodiments, the kits may include a commercially available implantable drug infusion system (including but not limited to the systems disclosed herein) and any component parts (e.g., catheters, etc.).

The kits can further include instructions for implantation into the cranium. In various embodiments, the instructions provide directions for implanting a device into a patient (including but not limited to the methods disclosed herein) and for using the device to treat a patient in need of neuromodulation therapy.

As explained in detail above, the systems and devices disclosed herein house neuromodulation devices (IPGs or drug infusion systems) inside the skull vault thereby eliminating or at least reducing the need for the connections (e.g., electrodes or catheter) associated with IPGs or drug infusion systems to be placed under the scalp or the skin, thereby reducing patient discomfort, potential failure of the device's (IPG or pump) hardware, or erosion of the patient's skin covering the device's parts or connections, and thereby reducing the risk of patient infection.

Those skilled in the art will appreciate that various adaptations and modifications of the above described embodiments may be configured without departing from the scope and spirit of this disclosure. By way of example, and not of limitation, it will be appreciated that the invention can be embodied in various forms which include but are not limited to the following:

1. A system for implantation of a neuromodulation device into a patient's cranium, the system comprising: (a) a neuromodulation device having at least one connection associated therewith; and (b) an implantable device comprising: (i) a device housing comprising a connection opening defined therein and configured to receive the at least one connection associated with the neuromodulation device, (ii) a cover, (iii) a connection holding cap configured to receive the at least one connection associated with the neuromodulation device and configured to be operably connected to the connection opening after receiving the at least one connection associated with the neuromodulation device, and (iv) a neuromodulation device holder operably connected to the implantable device and configured to receive the neuromodulation device and secure the neuromodulation device within the implantable device.

2. The system of embodiment 1, further comprising a connection clamp operably connected with the at least one connection associated with the neuromodulation device, wherein the connection clamp secures the at least one connection in a slot located at an outer circumference of the connection opening.

3. The system of embodiment 2, further comprising a connection clamp applicator for operably connecting the connection clamp to the connection opening.

4. The system of embodiment 1, further comprising at least one coupling device operably connecting the implantable device to the patient's cranium.

5. The system of embodiment 4, wherein the coupling device is a screw or a bolt.

6. The system of embodiment 1, wherein the neuromodulation device is an implantable pulse generator.

7. The system of embodiment 6, wherein the at least one connection associated with the neuromodulation device is an electrode.

8. The system of embodiment 1, wherein the neuromodulation device is an implantable drug delivery system.

9. The system of embodiment 8, wherein the at least one connection associated with the neuromodulation device is a catheter.

10. An implantable device configured for receiving a neuromodulation device, the device comprising: (a) a device housing comprising: (i) a connection opening defined therein, wherein the connection opening includes posts and slots and is configured to receive at least one connection associated with the neuromodulation device; (ii) a connection holding cap comprising posts, wherein the posts of the connection holding cap are configured to oppose the posts of the connection opening and wherein the connection holding cap is configured to receive the at least one connection associated with the neuromodulation device and configured to be operably connected to the connection opening by interconnecting the opposing connection holding cap and connection opening posts after receiving the at least one connection associated with the neuromodulation device; (iii) a neuromodulation device holder operably connected to the device housing and configured to receive the neuromodulation device and secure the neuromodulation device within the device housing; and (iv) a cover operably connected to the device housing and configured to close the device housing.

11. The device of embodiment 10, wherein the neuromodulation device is an implantable pulse generator.

12. The device of embodiment 11, wherein the at least one connection associated with the neuromodulation device is an electrode.

13. The device of embodiment 10, wherein the neuromodulation device is an implantable drug delivery system.

14. The device of embodiment 13, wherein the at least one connection associated with the neuromodulation device is a catheter.

15. The device of embodiment 10, wherein the device is a three-sided box shape, a three sided platform shape or dish-shaped.

16. A method for implantation of a neuromodulation device into a patient's cranium, the method comprising: (a) implanting in the patient's cranium an implantable device, the implantable device comprising: (i) a device housing having a connection opening defined therein, (ii) a neuromodulation device holder, (iii) a connection holding cap, and (iv) a cover; (b) introducing at least one connection associated with the neuromodulation device through the connection opening defined in the device housing; securing the connection about the connection opening; (c) operably attaching the connection holding cap to the connection opening; (d) introducing the neuromodulation device into the device housing; (e) operably connecting the neuromodulation device holder to a distal end of the device housing to secure the neuromodulation device within the neuromodulation device holder; and (f) operably connecting the cover to the device housing and the patient's cranium to close the implantable device.

17. The method of embodiment 16, wherein the neuromodulation device is an implantable pulse generator.

18. The method of embodiment 17, wherein the at least one connection associated with the neuromodulation device is an electrode.

19. The method of embodiment 16, wherein the neuromodulation device is an implantable drug delivery system.

20. The method of embodiment 19, wherein the at least one connection associated with the neuromodulation device is a catheter.

It should be noted that all directional references set forth herein (e.g., upper, lower, upward, downward, left, right, leftward, rightward, top, bottom, above, below, vertical, horizontal, clockwise, and counterclockwise) are relative and only used for identification purposes to aid the reader's understanding of the embodiments of the present invention, and are not limitations, particularly as to the position, orientation, or use of the invention unless specifically set forth in the claims. References to any joinder of elements (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

In some instances, components are described with reference to "ends" having a particular characteristic and/or being connected with another part. However, those skilled in the art will recognize that the present invention is not limited to components which terminate immediately beyond their points of connection with other parts. Thus, the term "end"

should be interpreted broadly, in a manner that includes areas adjacent, rearward, forward of, or otherwise near the terminus of a particular element, link, component, part, member or the like. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A system for implantation of a neuromodulation device into a patient's cranium, the system comprising:
    a neuromodulation device having at least one connection associated therewith adapted for operably connecting the neuromodulation device to a patient's brain; and
    an implantable device comprising:
        a device housing comprising a connection opening defined therein and configured to receive the at least one connection associated with the neuromodulation device, and upwardly-extending posts radially disposed about an outer circumference of the connection opening, adjacent ones of the posts defining slots therebetween, wherein the at least one connection passes through a respective slot, and
        a connection holding cap configured to receive the at least one connection associated with the neuromodulation device and configured to be operably connected to the connection opening after receiving the at least one connection associated with the neuromodulation device the connection holding cap including downwardly-extending posts radially disposed about an outer circumference of the connection holding cap, whereby each downwardly-extending post extends into a corresponding slot between an adjacent pair of the upwardly-extending posts, and
        a neuromodulation device holder operably connected to the implantable device and configured to receive the neuromodulation device and secure the neuromodulation device within the implantable device.

2. The system of claim 1, further comprising a connection clamp operably connected with the at least One connection associated with the neuromodulation device, wherein the connection clamp extends within a respective slot and secures the at least one connection in the respective slot to a respective adjacent pair of posts.

3. The system of claim 2, further comprising a connection clamp applicator for operably connecting the connection clamp to the respective adjacent pair of posts.

4. The system of claim 1, further comprising at least one coupling device adapted for operably connecting the implantable device to the patient's cranium.

5. The system of claim 4, wherein the coupling device is a screw or a bolt.

6. The system of claim 1, wherein the neuromodulation device is an implantable pulse generator.

7. The system of claim 6, wherein the at least one connection associated with the neuromodulation device is an electrode.

8. The system of claim 1, wherein the neuromodulation device is an implantable drug delivery system.

9. The system of claim 8, wherein the at least one connection associated with the neuromodulation device is a catheter.

* * * * *